United States Patent [19]

Hartmann

[11] Plant 4,377

[45] Feb. 13, 1979

[54] CHRYSANTHEMUM PLANT NAMED HARTMANN'S DIGNITY

[75] Inventor: Fred B. Hartmann, Kirkwood, Mo.

[73] Assignee: Pan-American Plant Company, West Chicago, Ill.

[21] Appl. No.: 837,744

[22] Filed: Sep. 29, 1977

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new white chrysanthemum selection of the standard chrysanthemum variety "Dignity" (U.S. Plant Pat. No. 3,309) particularly distinguished by its 2 to 4 day earlier flowering response, reflexing of ray florets upon reaching full maturation and averaging about 15% larger in bloom size when compared with the variety "Dignity".

3 Drawing Figures

BACKGROUND OF THE NEW PLANT

This new chrysanthemum was observed in July 1975 in a field of the standard chrysanthemum variety Dignity growing at Kirkwood, Mo., and was selected for propagation and test because of its early response compared with the Dignity plants with which it was growing.

Year around flowering of plants propagated at Kirkwood, Mo., by cuttings from the original plant and clones thereof has demonstrated that the distinctive characteristics of this new plant hold true from generation to generation and appear to be firmly fixed. This new plant has been and is now being propagated by vegetative cuttings at Kirkwood, Mo., West Chicago, Ill., and at Cortez, Fla., and its distinctive characteristics continue to hold true.

DESCRIPTION OF THE DRAWINGS

This new chrysanthemum plant is illustrated by the accompanying drawings in which sheet one shows two views comparing blooms of the new plant and the variety Dignity, both plants having been placed under short day photoperiodic conditions on the same date thus displaying the time difference in bloom development, FIG. 1 showing the flowers when Dignity was newly opened, the flower at the left being that of the new plant, and FIG. 2 showing the flowers when the new plant, shown at the right, reached full bloom; and sheet two showing typical leaves of the new plant at three stages of maturity.

FIG. 3, right view, shows the reflexed ray florets of the mature bloom of the instant variety.

DESCRIPTION OF THE NEW PLANT

Figure 2:
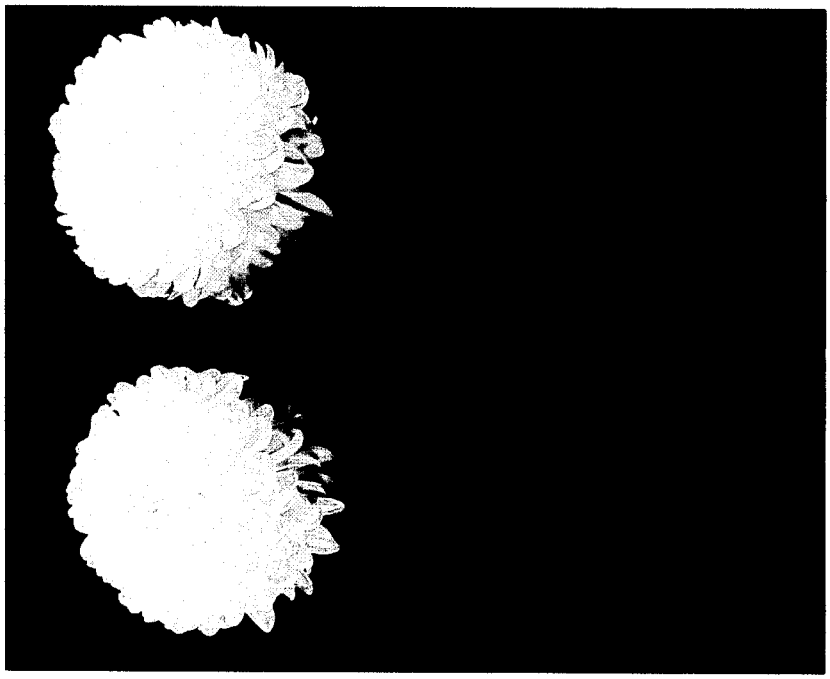
Figure 1:
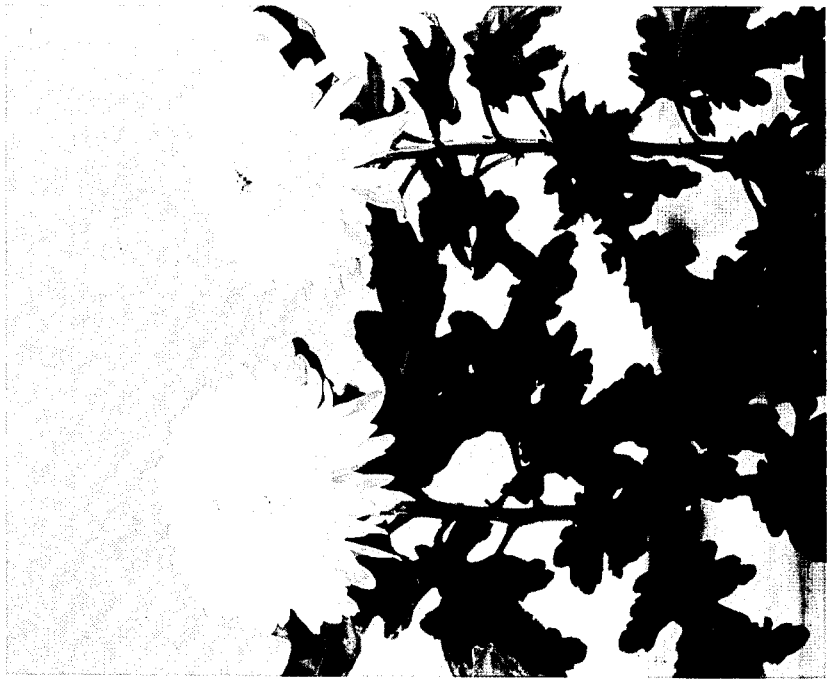

The following is a description of my new chrysanthemum selection, the color designations stated being according to the R.H.S. Colour Chart published by The Royal Horticultural Society of London, England.

THE PLANT

Origin: A selection from a field of the variety Dignity (U.S. Plant Pat. No. 3,309) growing under glass at Kirkwood, Mo.

Classification:

*Botanic.*—*Chrysanthemum morifolium.*

*Commercial.*—Standard incurved greenhouse cut flower.

Form: Perennial herbaceous upright bush.

Height: 40 to 48 inches when provided with 3 weeks of long-day photoperiodic treatment and optimum growing conditions.

Growth: Vigorous and sturdy with very good strength.

Branching: Normal, under natural conditions.

Foliage: Abundant, 7 to 9 leaves per 10 inches of stem.

*Leaf Size.*—Length — About 5⅜ to 8 inches. Width — About 2⅞ to 5 inches.

*Shape.*—Lobed, lanceolate and deeply serrated.

*Appearance.*—Canescent.

*Venation.*—Pinnate.

*Color.*—Upper side — Yellow-Green 147A. Under side — Yellow-Green 147B.

*Petioles.*—About ¾ to 1½ inches long.

THE BUD

Form: Globular.

Size:

*Diameter.*—About ⅝ to ¾ inch.

*Depth.*—About ⅜ to ½ inch.

Opening Rate: Slow.

Color:

*When phyllaries first divide.*—Yellow-Green 144B.

*When florets begin to unfurl.*—Yellow 2D, 6D.

Phyllaries: The outside of the receptacle bears many involucral bracts.

Shape: Spear-shaped.

Surface Texture: Pubescent.

Color:

*Inside.*—Yellow-Green 146A.

*Outside.*—Yellow-Green 148A.

Peduncle: Erect. About ¾ to 2½ inches long and with pubescent surface texture.

THE FLOWER

Blooming Period: Year around with photoperiod control.

Response: 9 week. Flower maturation occurs about 59 to 63 days after initiation of short-day photoperiodic treatment.

Natural Season Flowering: About October 27 to November 4.

Flower Type: Composite and incurved standard.

Borne: As a head of many florets on a receptacle; naturally raceme — singly when disbudded.

Size: Very large when fully opened.

*Diameter.*—About 5¼ to 6½ inches.

*Depth.*—About 3¼ to 5 inches.

Shape: Flat when bloom first opens becoming more globular as bloom matures.

Petalage: Florets are numerous with capitulum arrangement.

*Form.*—Linear and incurved with obtuse apex.

*Texture.*—Soft.

*Appearance.*—Very slight shine.

*Color.*—Outer florets — Upper and reverse sides White 155B at all seasons. Inside florets — Upper and reverse sides Yellow 2D at all seasons.

*Discoloration After Full Bloom.*—None.

Peduncle: Length — About ¾ to 2½ inches long.

*Strength.*—Sturdy and upright.

*Color.*—Yellow-Green 147C

Persistence: Florets hang on and dry.

Fragrance: Typical chrysanthemum.

Lasting Quality:

*On plant.*—3 weeks.

*As cut flower.*—10 to 14 days.

REPRODUCTIVE ORGANS

Stamens: Syngenesious and 5 in number.

*Anthers.*—Arrangement — Connate.

*Filaments.*—About 1/16 to ⅛ inch long.

*Color.*—Light Yellow.

*Pollen.*—Color — Yellow.

Pistils: One to each ray and disc floret.

*Styles.*—About ⅛ to 3/16 inch long.

*Stigmas.*—Yellow in color.

*Ovaries.*—Inferior and bicarpellate.

This chrysanthemum selection of the standard chrysanthemum variety Dignity is distinguished by its consistent several days earlier response and shorter internodes or stem length from leaf to leaf.

The following table is based upon observations of greenhouse plants bloomed during mid-Spring of 1978.

| | Dignity | Hartmann's Early Dignity |
|---|---|---|
| Bud | | |
| Diameter: | 5/8 inch | about 3/4 inch |
| Depth: | 3/8 inch | 3/8 to 1/2 inch |
| Opening: | slowly | slowly |
| Color: | 155B | 155B |
| Flowering | | |
| Response: | 62 to 67 days after start of bud | averaging about 59 to 63 days after start of bud |
| Foliage | | |
| Size: | average length 5-1/2 inches | 5-3/8 to 8 inches long |
| | average width 3-1/2 inches | 2-1/2 to 5 inches wide |
| Quantity: | 30 leaves/3 feet of stem | approx. 10% additional leaves per unit of stem length |
| Texture: | leathery and slightly glossy | same |
| Stem | | |
| Diameter: | av. 4/16 inch | generally about 1/16 inch larger |
| Length: | 42–52 inches when provided 3 weeks of long-day photoperiodic treatment | generally about 2–3 inches shorter with same long-day photoperiodic treatment |
| Blossom | | |
| Form: | incurved | incurved |
| Form change upon maturation: | none | petal reflexing |
| Size: | depth - 2-3/4 to 5 inches | depth - 3-1/4 to 5 inches |
| | diameter - 4-1/2 to 6-1/2 inches | diameter - 5-1/4 to 6-1/2 inches |
| Shape: | globular | globular |
| Color: | 155B | 155B |

I claim:

1. A selection of the chrysanthemum variety "Dignity" substantially as herein shown and described, characterized by its 2–3 inches shorter stem length (when provided 3 long-day weeks of photoperiodic treatment), 15 to 20% larger leaf size, approximately 10% shorter internodes, 2 to 4 days earlier flowering response, reflexing of ray florets upon full bloom maturation, approximately 1/16 inch larger stem diameter and approximately 15% larger bloom size compared to the standard "Dignity" plant.

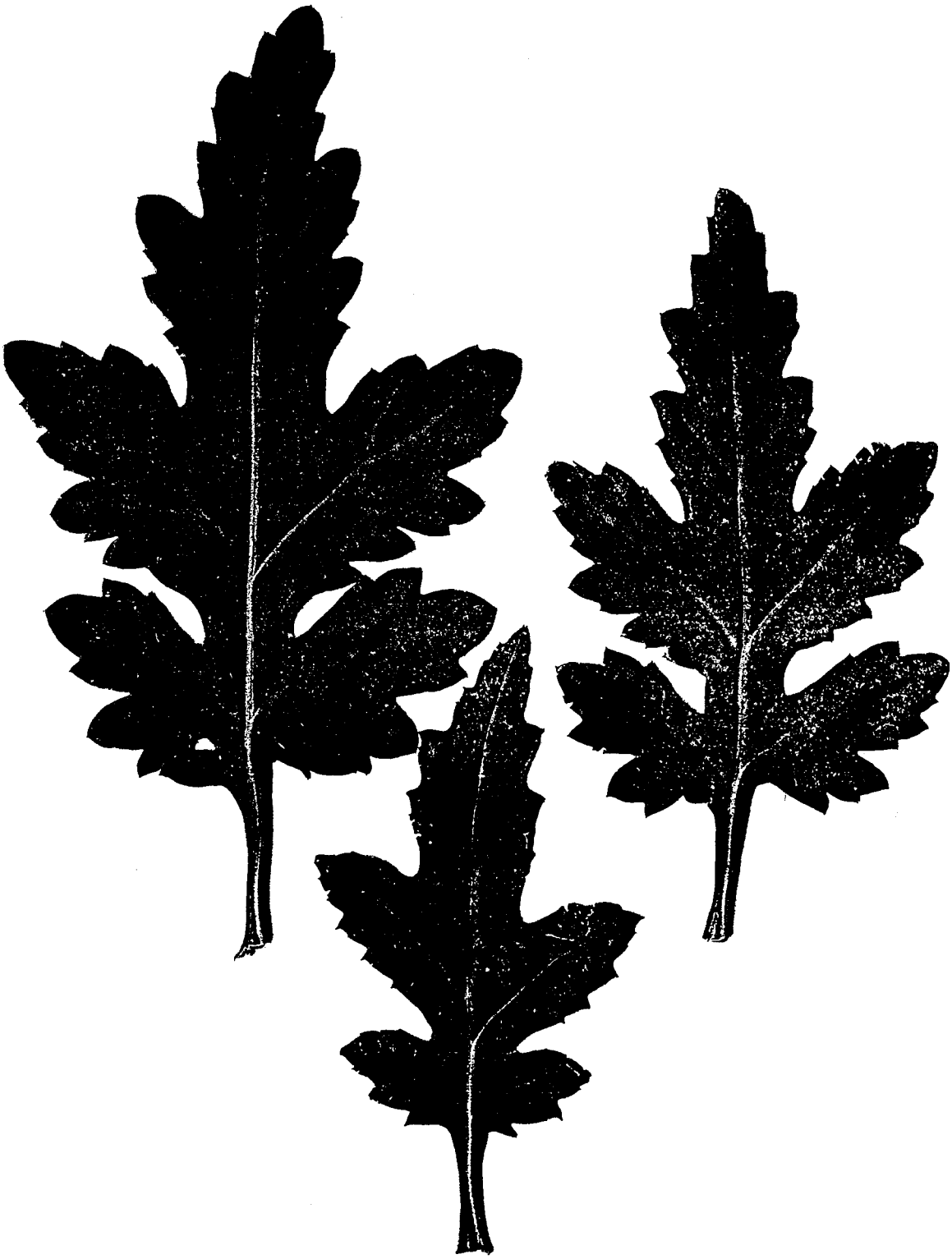

* * * * *